(12) United States Patent
Lewis et al.

(10) Patent No.: US 6,280,429 B1
(45) Date of Patent: Aug. 28, 2001

(54) GROSS FILTER FOR A DRAINAGE DEVICE

(75) Inventors: Anthony K. Lewis; David Rork Swisher, both of St. Charles; Eugene E. Weilbacher, Ellisville; Jacky S. Yam, St. Louis, all of MO (US)

(73) Assignee: Sherwood Services AG, Schaffhausen (CH)

( * ) Notice: Subject to any disclaimer, the term of this patent is extended or adjusted under 35 U.S.C. 154(b) by 0 days.

(21) Appl. No.: 09/205,909

(22) Filed: Dec. 4, 1998

Related U.S. Application Data (60) Provisional application No. 60/068,250, filed on Dec. 19, 1997.

(51) Int. Cl.$^7$ .......................... A61M 37/00; A61M 1/14; A61M 1/00; A61B 19/00; B01D 25/00
(52) U.S. Cl. ................ 604/406; 604/6.15; 604/4.01; 604/327; 422/44; 210/323.1; 210/346; 210/455; 210/445
(58) Field of Search .................. 604/413, 4.01, 604/6.15, 403, 406, 327, 356; 422/44; 210/252–53, 256, 257.1–257.2, 259–61, 321.64, 84, 322, 323.1, 340, 342, 346, 347, 455, 435, 453, 445, 348

(56) References Cited

U.S. PATENT DOCUMENTS

| | | | |
|---|---|---|---|
| 4,402,687 | * 9/1983 | Denty et al. | 604/319 |
| 4,631,050 | 12/1986 | Reed et al. | |
| 4,909,780 | 3/1990 | Ouriel et al. | 604/4 |
| 5,141,504 | 8/1992 | Herweck et al. | 604/317 |
| 5,401,262 | * 3/1995 | Karwoski et al. | 604/321 |
| 5,722,964 | * 3/1998 | Herweck et al. | 604/317 |
| 5,743,894 | 4/1998 | Swisher | 604/320 |
| 5,879,624 | * 3/1999 | Boehringer et al. | 422/44 |
| 6,099,493 | * 8/2000 | Swisher | 604/4.01 |

* cited by examiner

*Primary Examiner*—Angela D. Sykes
*Assistant Examiner*—Patricia Bianco
(74) *Attorney, Agent, or Firm*—Mark S. Leonardo; Peter B. Sorell; Brown Rudnick Freed & Gesmer (57) ABSTRACT

A gross filter in a drainage device for filtering fluids drained from the pleural cavity of a patient comprising a filter body having a first side panel, second side panel, back panel and bottom panel that assemble to form a generally box-shape filter with open front and top portions. The gross filter is located in the first of two subchambers that comprise the collection chamber. The filter body further comprises a filter screen sized for filtering gross particulates, such as blood clots, that may become entrained in fluid drained from a patient. The gross body is configured so as to permit the further filtering of fluids when blood clots have formed and blocked the filter screen of the filter's bottom panel from fluid flow therethrough, thereby allowing uninterrupted filtering of blood into the collection chamber through the first and second side panels instead. To further facilitate the filtering of blood through the filter body when a blocked state exists at the bottom panel portion thereof, the first and second side panels are angled toward each other at their bottom ends and gradually spaced apart from the collection chamber walls in order to permit unimpeded filtering of fluid through the side panels. The open front portion of the gross filter permits clear viewing by medical personnel of the amount of blood clots being retained inside the filter body so that measuring indicia may be provided on the drainage unit's front panel as an indication of the amount and rate of blood clot retention inside the filter. An overflow filter portion is also provided at the top portion of one of the side panels for filtering fluid when the rest of the filter body is clogged and blocked by blood clots or when the first subchamber is filled to capacity.

21 Claims, 11 Drawing Sheets

GROSS FILTER FOR A DRAINAGE DEVICE

CROSS-REFERENCE TO RELATED APPLICATION

This patent application claims priority to U.S. Provisional Application Ser. No. 60/068,250, filed in the U.S. Patent and Trademark Office on Dec. 19, 1997, by Lewis et al., the contents of which are incorporated herein by reference in their entirety.

BACKGROUND OF THE INVENTION

1. Field of the Invention

The present invention relates to an improved filter, and more particularly to a gross filter for use in a drainage device. Specifically, the present invention relates to a gross filter with an open face that is configured to lessen filter blockage by gross particulate matter, for example blood clots, entrained in incoming fluid while also permitting a clear view of blood clot volume retained inside the filter.

2. Prior Art

Gross filters for use in filtering out large particulate matter entrained in body fluids drained from a patient during convalescence or post-operative recovery are well known in the art. Typically, gross filters of this kind are incorporated in a drainage device, for example a Chest Drainage Unit (CDU), for filtering blood clots and other gross contaminates from body fluids before reinfusing such fluids back to the patient.

A CDU is an apparatus for suctioning gases and liquids from the pleural cavity of a patient in order to re-expand the patient's lungs. The pleural cavity lies within the rib cage above the diaphragm and is surrounded by the pleural membrane. The pleural cavity contains both lungs, which in their normal expanded state fill the pleural cavity. Several conditions and diseases such as interventional surgery, trauma, emphysema and various infections can cause a build up of liquid and gases around the lungs in the intrapleural space. When this happens, it causes the lungs to collapse to a volume much less than that of the pleural cavity, thereby severely impairing breathing functions of the patient. The lungs can be re-expanded to their normal state to fill the pleural cavity by draining the liquid and gases from the intrapleural space using the CDU. A typical CDU and its operation is disclosed in U.S. patent application Ser. No. 08/810,056 to Swisher et al. entitled "Chest Drainage Unit with Controlled Automatic Excess Negativity Relief Feature", assigned to the assignee, and is herein incorporated by reference in its entirety.

During the draining of fluid from a patient's pleural cavity blood clots may develop and become entrained in the fluid as it enters the collection chamber of the CDU for eventual reinfusion to the patient. During reinfusion of blood, it is desirable that the collected blood be free of any large particulate matter or other kinds of gross contaminants before entering and collecting at the bottom portion of the collection chamber. In order to screen out these undesirable contaminants a gross filter is provided near the inlet to the collection chamber for filtering out large particulate matter as fluid enters the CDU. The Swisher et al. device referenced above is generally exemplary of medical drainage devices that incorporate a gross filter for filtering out blood clots and other large particulate matter from fluid drained from a patient's pleural cavity. The gross filter used in the Swisher et al. device comprises a porous filtering material placed near the inlet of the collection chamber in a horizontal orientation so that all incoming fluid must pass through the gross filter before collecting in a pooling area located at the bottom portion of the collection chamber. In this manner, incoming fluid is filtered prior to entering the pooling area so that blood clots and other large particulate matter are retained on top of the filter.

Unfortunately, the gross filter of the Swisher et al. device suffers from several drawbacks. First, blood clots that are filtered out and retained inside the gross filter will begin to block and impede the flow of fluid being filtered as blood clots begin to accumulate and spread over the surface area of the filter, thereby wasting blood that could be reinfused back to the patient. Second, the gross filter of the Swisher et al. device is made from a reticulated foam material which has a tendency to separate into smaller fragments when trimmed for the size required to properly fit into the collection chamber, thus causing possible contamination of already filtered fluid by these separated fragments.

As of yet, nothing in the prior art has addressed the problem of developing an improved gross filter made of a solid unitary construction that advantageously prevents total blockage of the filter by gross contaminants while also addressing the need for a gross filter that permits clear viewing and accurate visual measurement by medical personnel of the volume level of gross contaminants retained in the filter.

OBJECTS AND SUMMARY OF THE INVENTION

The principal object of the present invention is to provide a gross filter having a configuration that inhibits or prevents the total blockage of the filter by large particulate matter and other contaminants.

Another object of the present invention is to provide a gross filter that filters out large particulate matter, for example blood clots, before collection in the collection chamber.

A further object of the present invention is to provide a gross filter that permits clear visual measurement by medical personnel of the amount of large particulate matter and other gross contaminants retained inside the filter.

Another principal object of the present invention is to provide a means for channeling incoming fluid through a portion of the gross filter in order to prevent total blockage of the gross filter.

These and other objects of the present invention are realized in the preferred embodiment of the present invention, described by way of example and not by way of limitation. The preferred embodiment provides for a gross filter comprising a bottom panel, two side panels, and a back panel that collectively form a filter body having a generally rectangular cross-section. The filter body is configured so as to have open top and front portions, angled back and side panels, and a slanted bottom panel that forms an angled slope towards one end of the gross filter. Alternatively, the gross filter may have other shapes that include, but are not limited to, semicircular/conical or diamond shaped, with open front and top portions, which are suitable for filtering gross contaminants from incoming fluid.

The angled back and side panels of the filter body are configured so as to prevent total blockage of the filter body by channeling blood clots to one end thereof. The back and side panels are configured such that gravity will force blood clots to one portion of the gross filter due to their set angle. This type of angled configuration ensures a sufficient filtration rate through the gross filter when the bottom panel is partially or totally blocked with large particulate matter and promotes a maximum filtration rate when there is no blockage of the filter body present. A guide is provided on the interior portion of the gross filter's back panel for channeling incoming fluid toward one portion of the gross filter in order further prevent total blockage. A gutter ledge is provided along the top portion of the back panel for channeling incoming fluid towards one portion of the filter body that contacts the top portion of the back panel between the guide and the side panel under the inlet port.

The open front portion of the gross filter is positioned adjacent a partially transparent front wall of the CDU and allows for unobstructed viewing of the interior portion of the gross filter when large particulate matter entrained in incoming fluid are screened out and retained therein. Where large particulate matter has blocked the back, side and back panels of the gross filter, an overflow panel is provided for filtering fluid that overflows the interior portion of the gross filter or when the overflow of the entire first subchamber occurs.

The gross filter of the present invention is adapted for placement adjacent or near the inlet port inside a collection chamber of a drainage device, such as a CDU, for filtering incoming fluid of large particulate matter and other gross contaminates entrained therein. Preferably, the CDU is of the type that includes a collection chamber that comprises two or more subchambers that communicate through an overflow port with the gross filter located so that incoming fluid is filtered into the first subchamber and overflow fluid is filtered into the second or additional subchambers, if required. The gross filter is disposed inside the first subchamber and retained therein by an arrangement of grooves and a support member that are adapted to engage retaining ledges formed on the gross filter such that the front edges of both side panels of the gross filter are positioned flush against the front wall of the CDU. The portion of the front wall of the CDU in the area where the gross filter is located includes a clear viewing area of the interior portion of the gross filter and is provided with appropriate indicia adapted for accurate visual measurement of the volume of large particulate matter retained inside the interior portion of the gross filter by a user. A splash guard is provided on the interior portion of the first subchamber near the inlet port for channeling incoming fluid from the inlet port between the guide and the side panel so that incoming fluid is not allowed to freely flow into the gross filter. This channeling of incoming fluid by the splash guard and guide acting together prevents total blockage of the filter body. The gross filter further comprises an overflow portion that is positioned such that fluid that overflows through the first subchamber is filtered before entering the second subchamber.

DETAILED DESCRIPTION OF THE INVENTION

Figure 1:
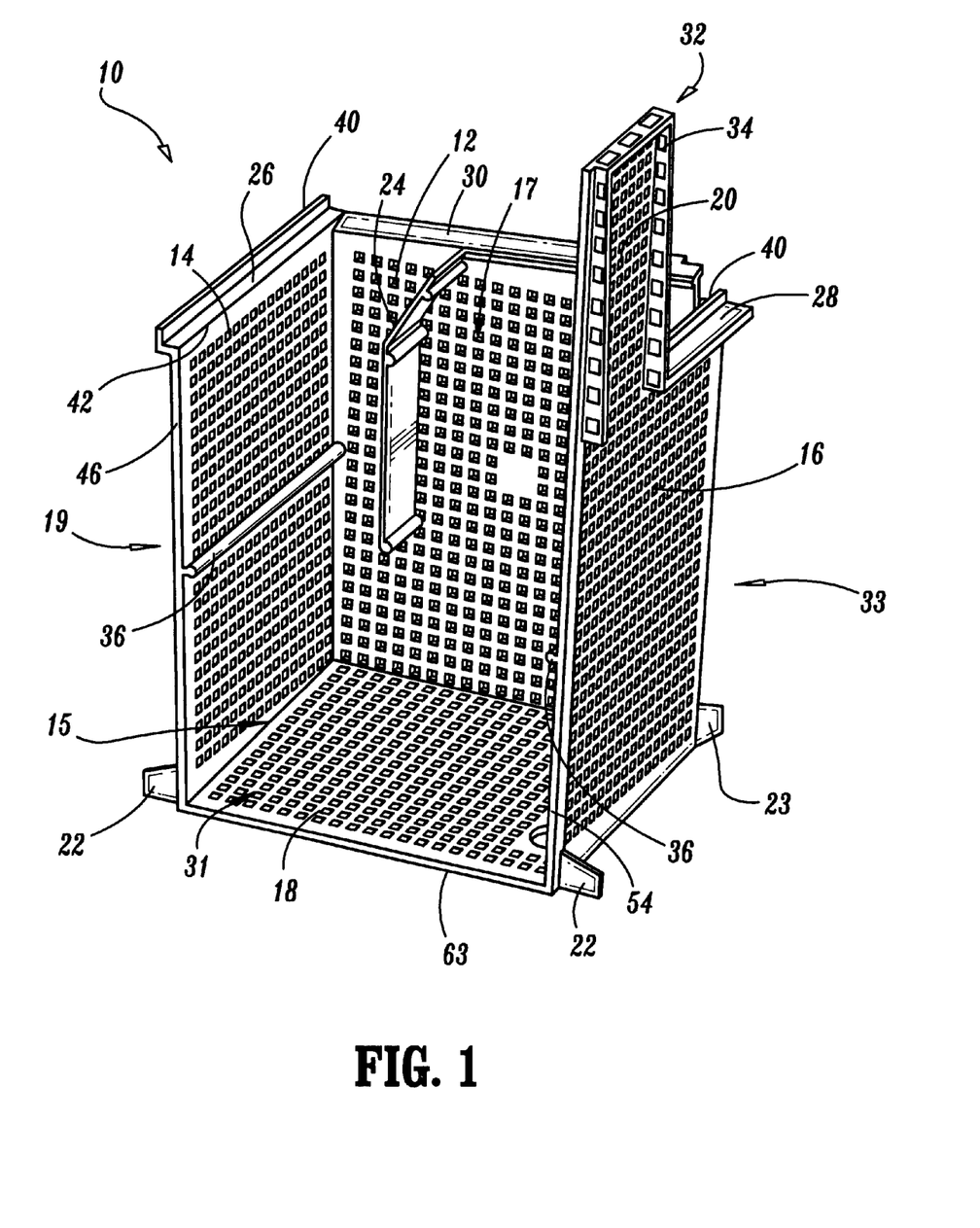
FIG. 1 is a perspective view showing the preferred embodiment of the gross filter according to the present invention.

Referring to the drawings, the preferred embodiment of the gross filter of the present invention is illustrated and generally indicated as 10 in FIG. 1. As shown in FIG. 1, gross filter 10 includes a filter body 19 that comprises a back panel 12, first and second side panels 14 and 16, bottom panel 18, and open front and top portions 15 and 17. Gross filter 10 is disposed inside a Chest Drainage Unit 11 (CDU) (FIG. 7) for filtering incoming fluid drained from a patient. Preferably, CDU 11 is a drainage device as disclosed in U.S. patent application Ser. No. 08/810,056 entitled "Chest Drainage Unit with Controlled Automatic Excess Negativity Relief Feature", assigned to the assignee, and is incorporated by reference in its entirety.

Figure 2:
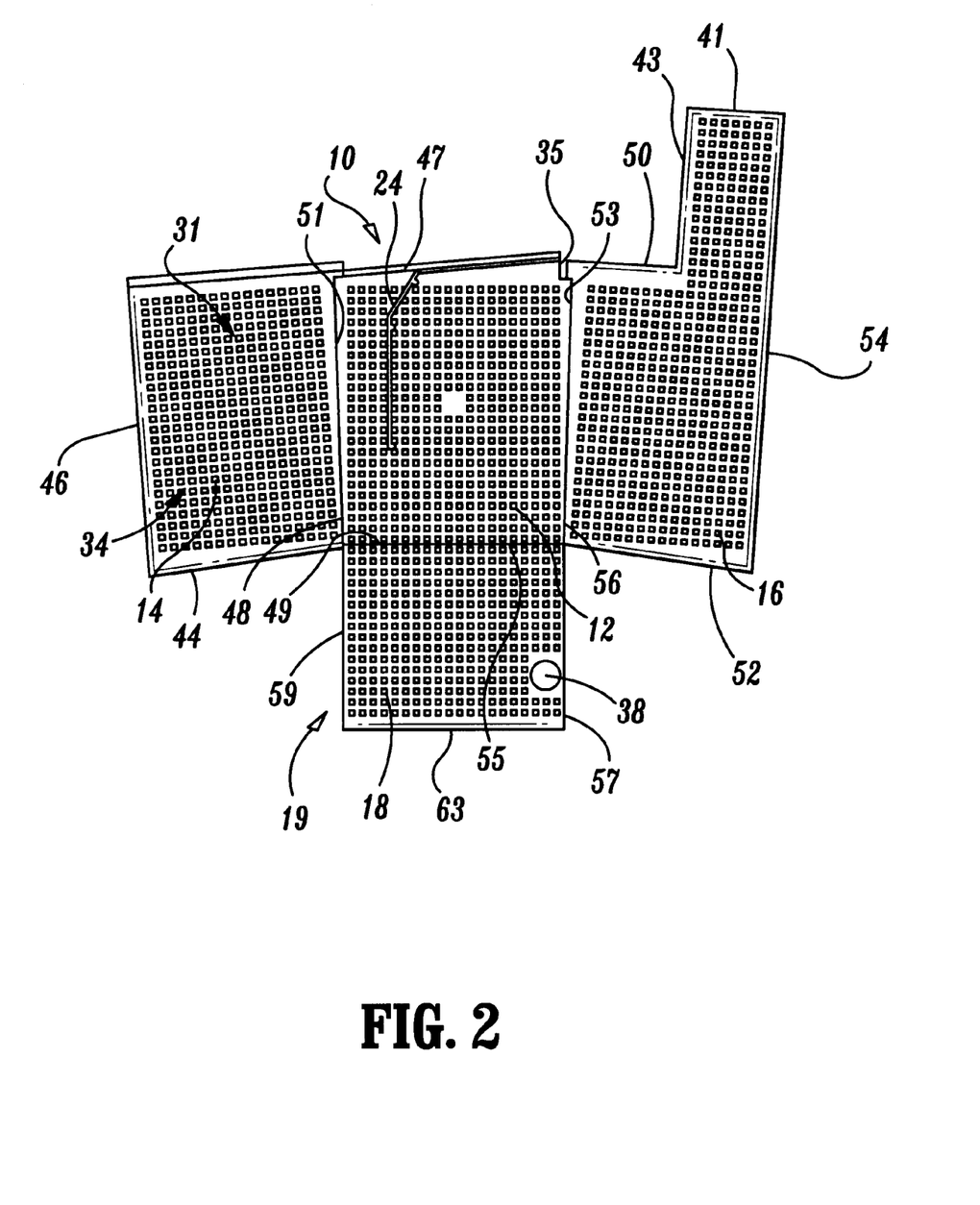
FIG. 2 is a plan view of the various panels that comprise the gross filter shown in FIG. 1 according to the present invention.

Referring to FIG. 2, a plan view of the panels 12, 14, 16 and 18 showing the interior side 31 of gross filter 10 is shown. Each panel 12, 14, 16 and 18 comprises a filter matrix 34 having a porosity sufficient for filtering fluid, for example blood, of blood clots and other gross contaminates as fluid passes through filter body 19. Preferably, filter matrix 34 includes, but is not limited to, a continuous pattern of rectangular or square-shaped designs, although any pattern, such as triangles, diamonds, circles, or crosses, which are suitable for filtering fluid of gross contaminates is felt to fall within the scope of the present invention.

Gross filter 10 comprises a generally rectangular-shaped planar back panel 12 defined by angled head edge 47, base edge 49, and generally angled opposing inner edges 51 and 53. A guide 24 is provided along the interior surface 31 for channeling incoming fluid to a specific portion of gross filter 10 in order to prevent total blockage of the filter body 19 by channeling any blood clots that are entrained in incoming fluid toward one portion of body 19. Preferably, both inner edges 51 and 53 extend away from base edge 49 at approximately 100 degree angle, although the angle may range between 90 and 120 degrees. Head edge 47 extends away from inner edge 51 at approximately a 90 degree angle where edge 47 terminates in a notch 35.

Inner edge 51 may be integrally formed with or attached to inner edge 48 of first side panel 14. First side panel 14 is located adjacent to back panel 12 and is defined by head edge 42, angled base edge 44, free edge 46 and angled inner edge 48. Base edge 44 extends away from inner edge 48 at approximately a 100 degree angle. Although the angle formed between base edge 44 and inner edge 48 is preferably 100 degree angle, the angle may range between 90 and 120 degrees.

Inner edge 53 of back panel 12 may be integrally formed with or attached to inner edge 56 of second side panel 16. Opposed to first side panel 14 with respect to back panel 12 is second side panel 16 which is defined by free edge 41, left free edge 43, head edge 50, angled base edge 52 and right free edge 54. Head edge 50 extends away from inner edge 56 at an 85 degree angle, although the angle may range between 90 degrees and 75 degrees. Preferably, base edge 52 extends away from inner edge 56 at a 100 degree angle, although the set angle may range between 90 and 120 degrees.

Base edge 49 may be integrally formed with or attached to head edge 55 of bottom panel 18. Bottom panel 18 is located adjacent to back panel 12 and is defined by head edge 49, opposed right and left free edges 57 and 59, and base edge 63. An opening 38 is formed through the bottom panel 18 for receiving therethrough a conduit for the egress of fluid from collection chamber 13.

As illustrated back in FIG. 1, first and second side panels 14 and 16 may include a reinforcing bar 36 that extends the entire length of each panel 14 and 16 from the back panel 12 to free edges 46 and 54, respectively, and provides structural reinforcement to filter body 19. Each side panel 14 and 16 further includes a side spacer 22 that is spaced slightly inward from free edges 46 and 54 and extends in perpendicular relationship to the exterior surface 33 of each respective side panel 14 and 16. Second side panel 16 comprises an overflow portion 20 that extends from the main body of panel 16 and is adapted to filter any fluid that may overflow from gross filter 10. Overflow portion 20 includes a filter matrix 34 that extends in perpendicular relation from overflow portion 20 and borders the entire periphery of portion 20. Overflow filter 32 provides additional filtering for initially filtered fluid that flows from between the filter body 19 and the wall of the collection chamber, as shall be explained in greater detail later.

First side panel 14 further comprises a first retaining ledge 26 along head edge 42 (FIG. 3) that includes a flange 40 that extends in perpendicular relationship with respect to ledge 26. As shall be explained in greater detail below, first retaining ledge 26 provides a connection site for securely retaining gross filter 10 inside CDU 11. Similarly, second side panel 16 includes a second retaining ledge 28 along head edge 50 (FIG. 4) that runs along the upper portion of panel 16 until ledge 28 meets overflow portion 20. Second retaining ledge 28 also forms a flange 40 that is in perpendicular relationship to ledge 28 and is adapted to securely retain gross filter 10 inside CDU 11.

As shall be illustrated later, bottom panel 18 slants downward from back panel 12 to base edge 63 of bottom panel 18 so as to channel fluid flow through specific portions of filter body 19 and inhibit free flow therethrough. The channeling of incoming fluid prevents total blockage of back panel 12 by forcing blood clots toward the front end of bottom panel 18 near base edge 63 so more accurate graduations of accumulated blood clots can be made by the user while leaving the remaining portion of panel 12 unblocked for filtering of incoming fluid. The upper portion of back panel 18 includes a gutter ledge 30 which is set at an angle that runs from first side panel 14 to notch 35 (FIG. 2) so that incoming fluid that is captured by ledge 30 gravity flows toward the first side panel 14 end of ledge 30 and then flows down between guide 24 and first side panel 14. Gutter ledge 30 effectively forms a conduit adapted for capturing incoming fluid along the back portion of filter body 19 and channeling it towards one end of body 19.

Figure 3:
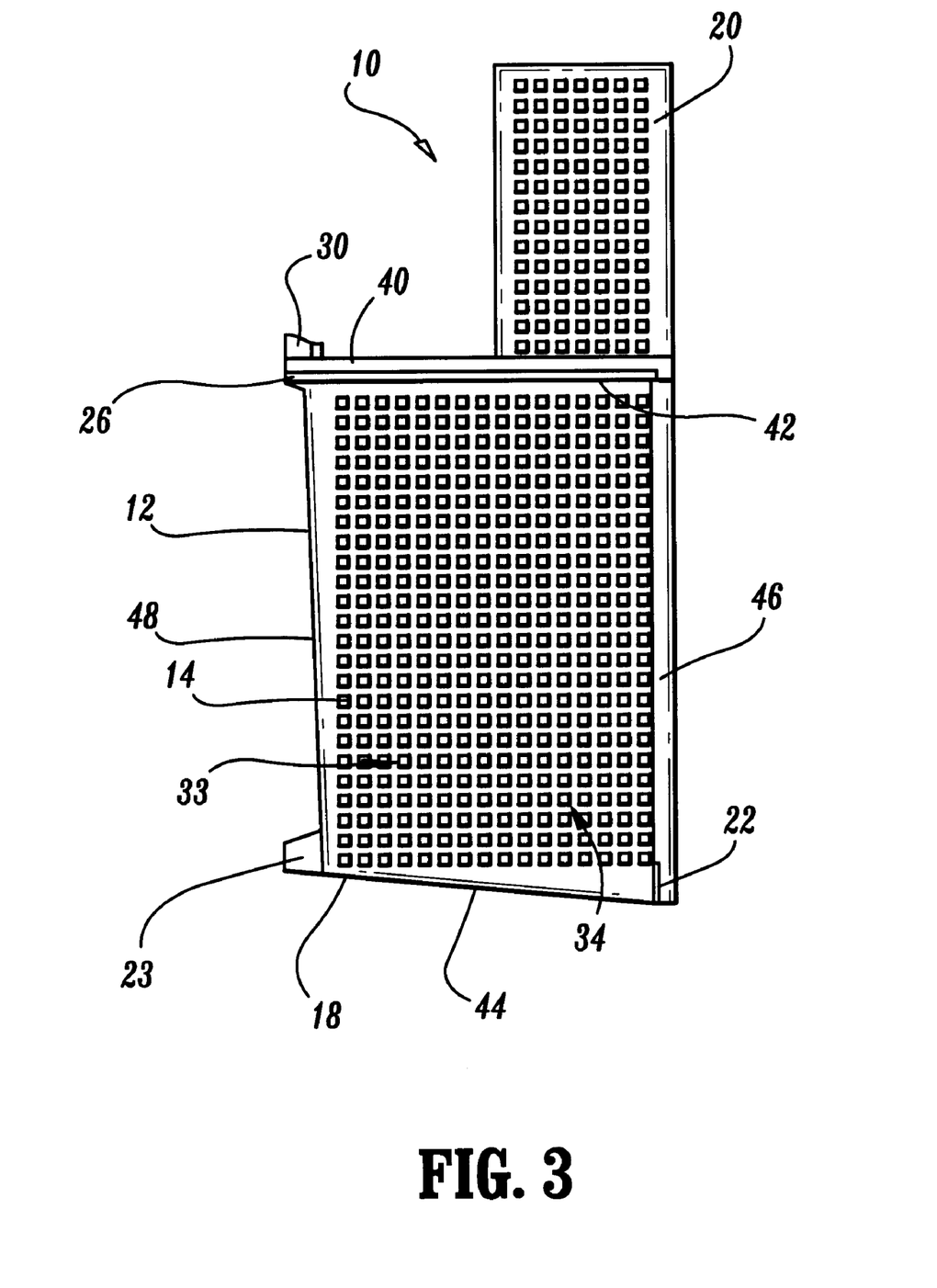
FIG. 3 is a side view of the gross filter shown in FIG. 1 illustrating the angled bottom and back panels according to the present invention.
Figure 4:
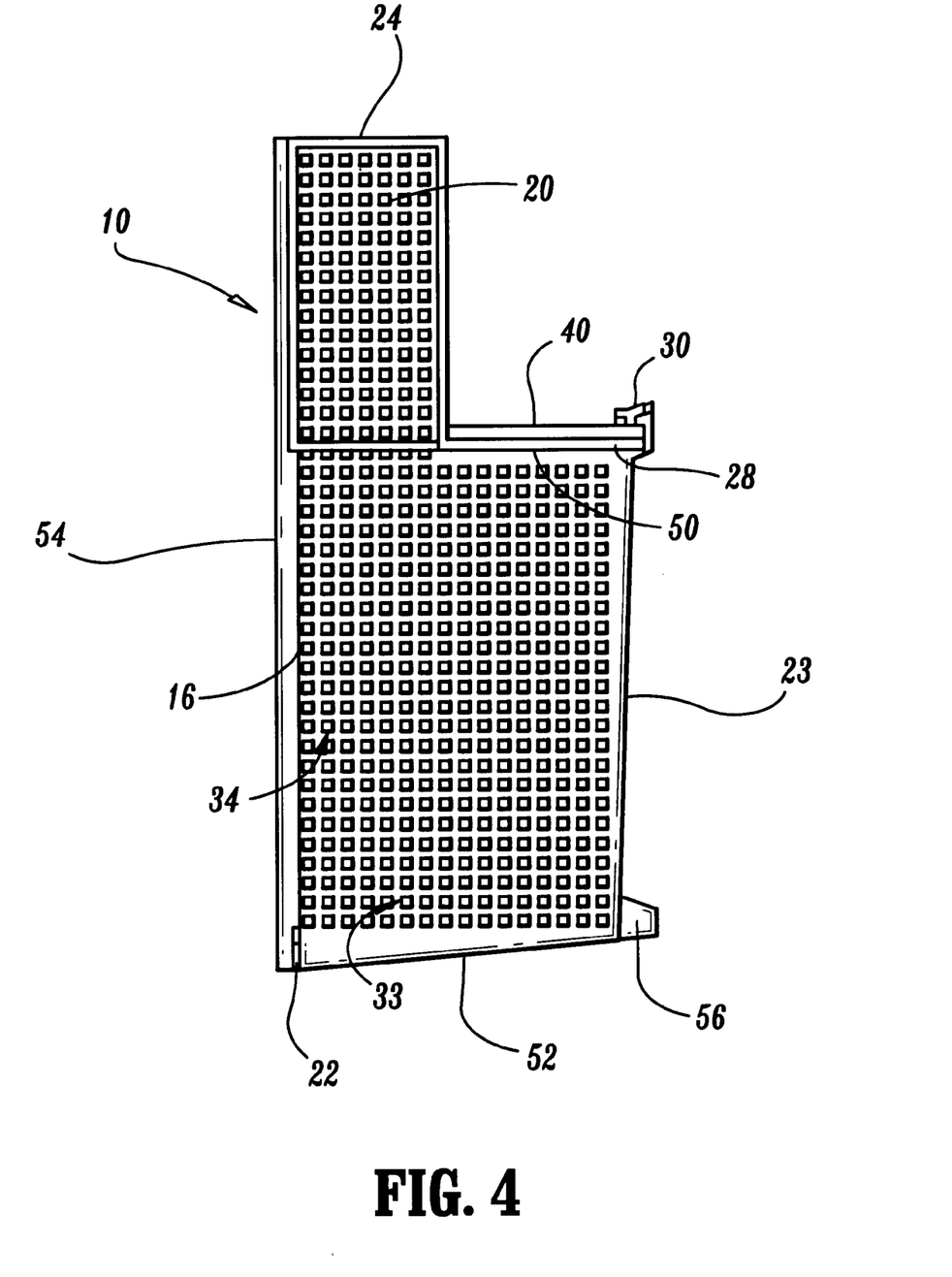
FIG. 4 is a side view of the gross filter shown in FIG. 1 illustrating the overflow portion of the gross filter according to the present invention.

Referring to FIGS. 3 and 4, opposite side views of gross filter 10 are shown illustrating the angled orientations of back panel 12 and bottom panel 18. Inner edges 48 and 56 of first and second side panels 14 and 16, respectively, are both set at the same angle in relation to free edge 46 and right free edge 54. As such, back panel 12 has a set angle that exposes the interior surface area of panel 12 to filtering of incoming fluid as it enters CDU 11 and passes through filter body 19.

As further illustrated in FIGS. 3 and 4, base edges 44 and 52 of first and second side panels 14 and 16, respectively, are set at the same angle such that bottom panel 18 forms a flat surface angled toward the open front portion 15 (FIG. 1). This angled orientation of bottom panel 18 forces blood clots and other gross contaminants towards the open front portion 15 of filter body 19, thereby leaving the back end portion of panel 18 unblocked. This sloped orientation of bottom panel 18 exposes a larger area of panel 18 to filtering of incoming fluid so that sufficient area of panel 18 is provided for filtering when other areas of panel 18 become clogged by blood clots and other large particulate matter retained inside filter body 19.

Figure 7:
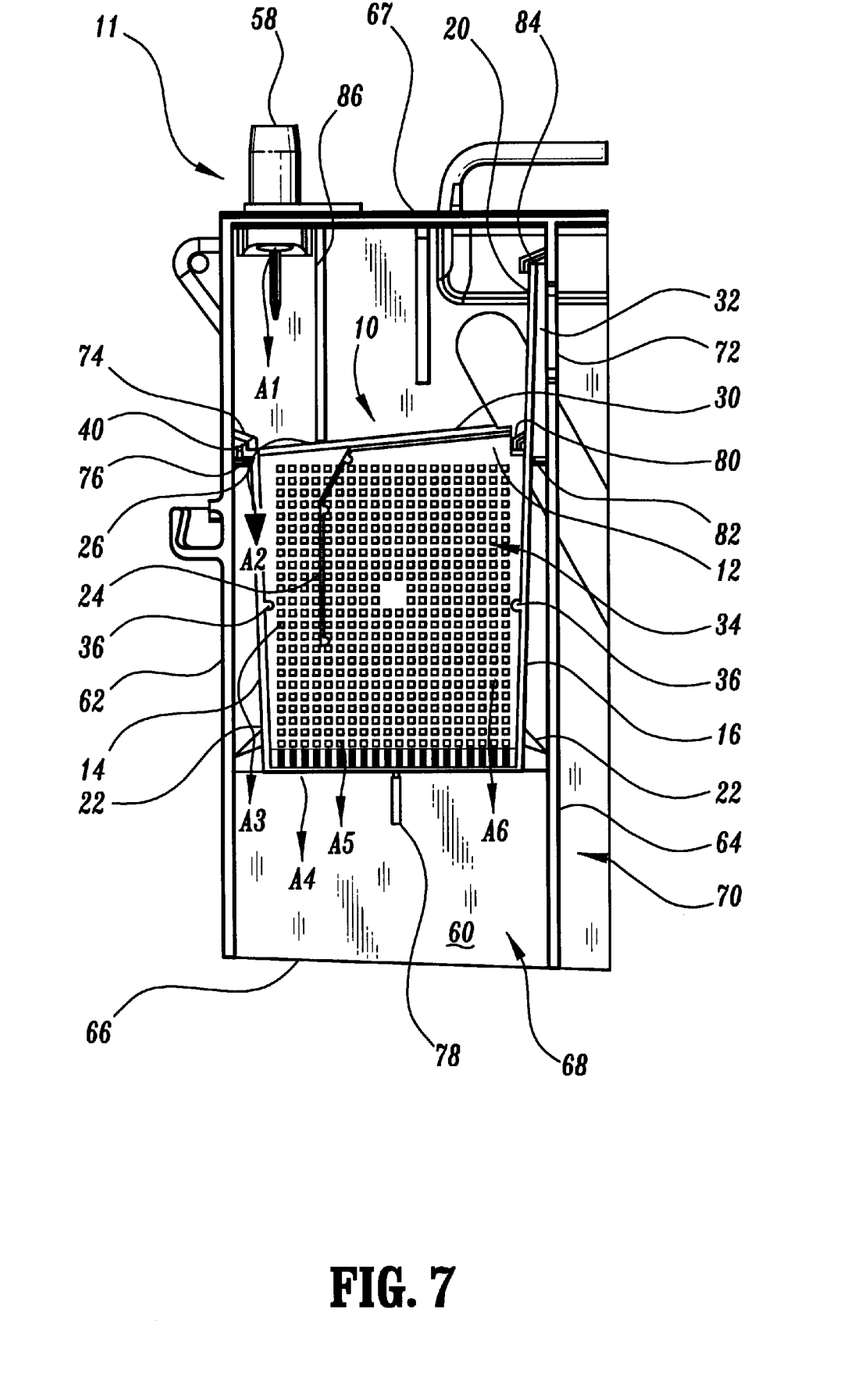
FIG. 7 is a front view of the gross filter shown in FIG. 1 disposed in the first subchamber of the Chest Drainage Unit illustrating the various flow pathways according to the present invention.

As illustrated in FIG. 7, first and second side panels 14 and 16 are preferably set at an angled orientation to one another so that the bottom portions of both panels 14 and 16 are angled slightly toward each other. However, other angled orientations such as having the top portion of first and second side panels 14 and 16 angled toward each other or having just one side panel 14 or 16 angled either toward or away from the other panel 14 or 16, which remains straight, is felt to fall within the scope of the present invention. The angled orientation of the first and second side panels 14 and 16 provide alternative filtration sites to incoming fluid flow.

Figure 8:
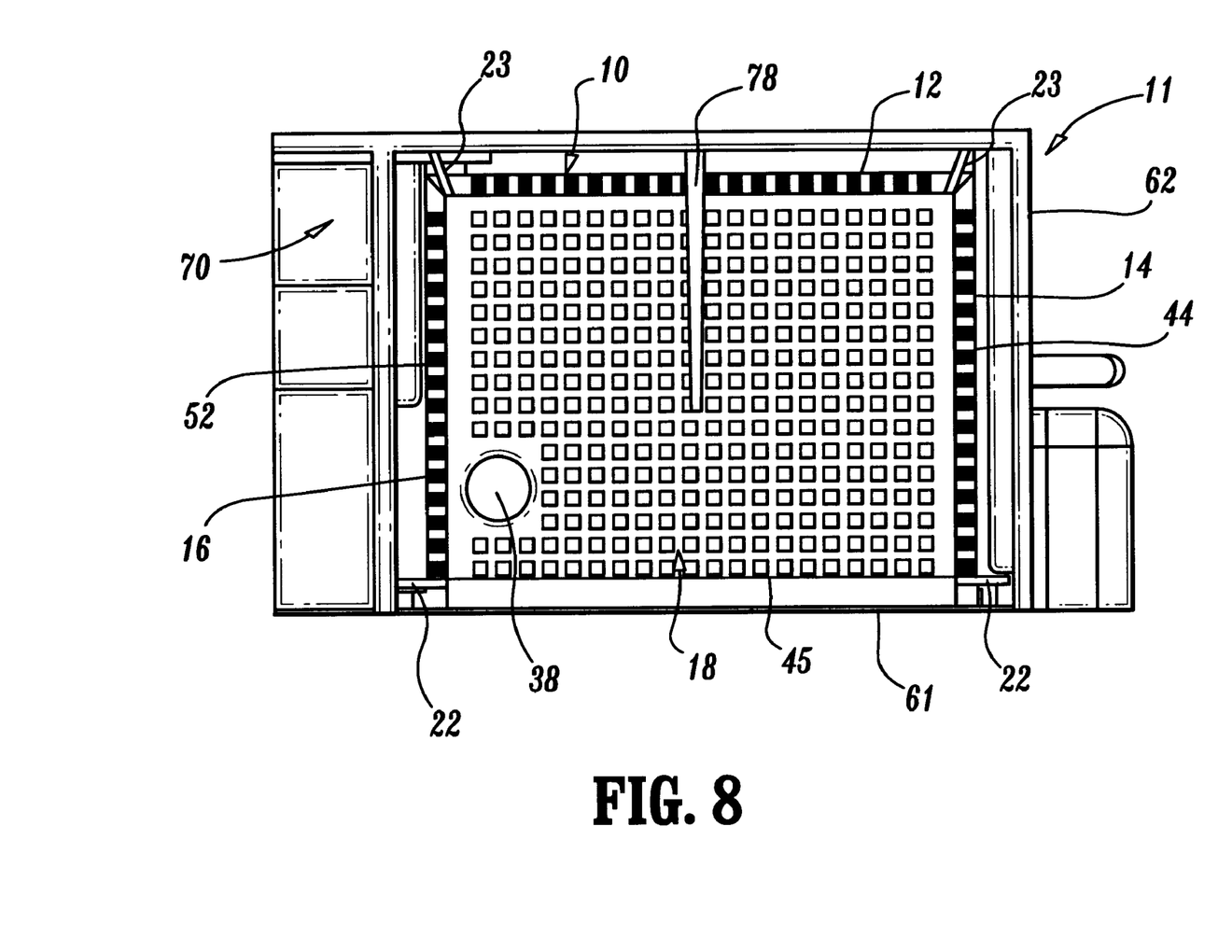
FIG. 8 is a bottom view of the gross filter shown in FIG. 6 according to the present invention.

Referring to FIG. 8, bottom panel 18 will be discussed in greater detail. An opening 38 is formed through bottom panel 18 and is adapted for receiving a conduit (not shown) therethrough for the transport of filtered fluid from collection chamber 13. In order properly orientate gross filter 10 inside collection chamber 13 during insertion of the filter into CDU 11 during manufacturing, a pair of side and back spacers 22 and 23, respectively, are provided along the bottom portion of first and second side panels 14 and 16. Side spacers 22 are integrally formed with or attached to the front portion of bottom edges 44 and 52, respectively, using a suitable adhesive, and extend therefrom in a perpendicular relation to each panel 14 and 16, so that lateral movement against the walls of the collection chamber 13 is prevented. Back spacers 23 are also integrally formed with or attached to the back portion of bottom edges 44 and 52, respectively, and are at a set angle in relation to back panel 12, so as to prevent backward and forward motion of filter body 19 inside CDU 11. Preferably, the angle set for back spacers 23 is 110 degrees in relation to back panel 12, although any angle between 50–120 degrees is felt to fall within the scope of the present invention.

Figure 5:
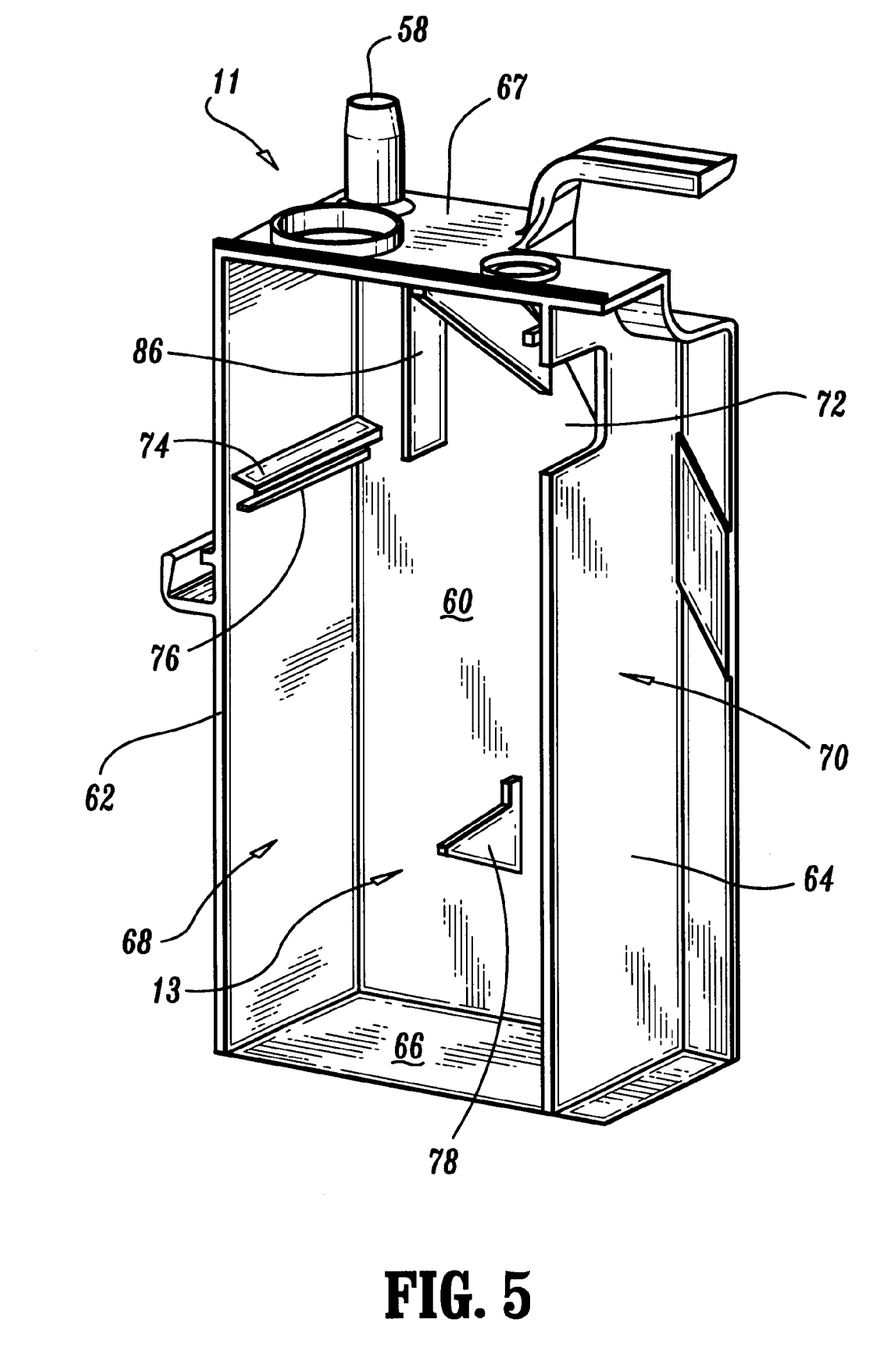
FIG. 5 is a partial cut-away of the first and second subchambers of the Chest Drainage Unit illustrating the groove and support member arrangement used to retain the gross filter shown in FIG. 1 inside the first subchamber according to the present invention.
Figure 6:
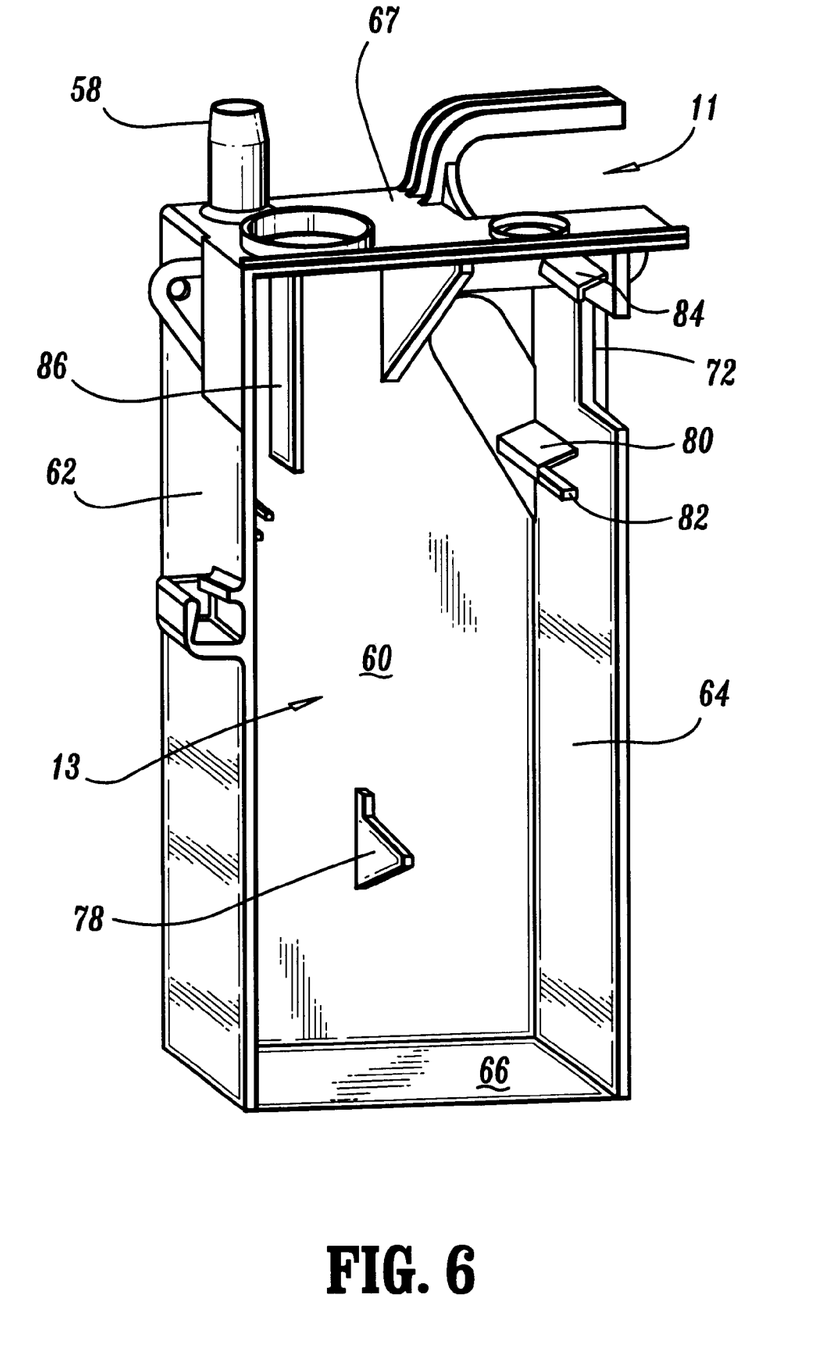
FIG. 6 is a partial cut-away of the first subchamber of the Chest Drainage Unit illustrating the groove and support member arrangement used to retain the gross filter shown in FIG. 1 inside the first subchamber according to the present invention.

Referring to FIGS. 5 and 6, the interior portions of CDU 11 which house gross filter 10 will be discussed in greater detail. CDU 11 comprises a collection chamber 13 that includes first subchamber 68 in fluid flow communication with a second subchamber 70 through an overflow panel 72 formed therebetween. First subchamber 68 comprises opposing first and second side walls 62 and 64, back wall 60, front wall 61 (FIG. 9), top wall 67 and bottom wall 66. An inlet port 58 adapted for permitting fluid flow into first subchamber 68 is formed through top wall 67.

Gross filter 10 is housed and securely retained inside first subchamber 68 through an arrangement of grooves formed on the interior surfaces of first and second side walls 62 and 64 of first subchamber 68. A first upper groove 74 in combination with a first lower groove 76 are provided on the first side wall 62 and are adapted to engage first retaining ledge 26 of first side panel 14. Similarly, a second upper groove 80 in combination with a second lower groove 82 are provided on second side wall 64 and are adapted to engage second retaining ledge 28 of second side panel 16. A third groove 84 is provided above the third upper and lower grooves 80 and 82 and is adapted to retain overflow portion 20 of second side panel 16 when gross filter 10 is housed inside first subchamber 68.

During manufacturing gross filter 10 is inserted into first subchamber 68 before the front wall 61 is attached to CDU 11. To engage and retain gross filter 10 inside first subchamber 68, retaining ledges 26 and 28 of gross filter 10 are inserted through and engaged to grooves 74, 76 and 80, 82, respectively, formed on the first and second sidewalls 62 and 64 of first subchamber 68. As shown in FIG. 7, flanges 40 of first and second retaining ledges 26 and 28 are inserted through the respective slots formed between the upper and lower grooves 74 and 76 and upper and lower grooves 80 and 82. Concurrently, overflow panel 32 is inserted through the slot formed by third upper groove 84 so that gross filter 10 is securely retained inside first subchamber 68 and flush against the front portion of CDU 11. A support member 78 (FIGS. 5, 6 and 8) forming a straight lateral ledge extending from back wall 60 is provided for supporting bottom panel 18 of filter body 19 inside first subchamber 68 once body 19 has been inserted therein. Once gross filter 10 has been inserted and retained inside CDU 11, the front wall 61 is attached to the front portion of CDU 11 using an adhesive bond or other suitable means of attachment including, but not limited to, ultrasonic welding or riveting.

Referring to FIG. 7, the fluid flow pathway of incoming fluid into first subchamber 68 and through gross filter 10 is illustrated. Flow pathway A1 demonstrates the path of incoming fluid directly into collection chamber 13 as incoming fluid is channeled downward by splash guard 86 through the open top portion of filter body 19. As discussed above, once incoming fluid enters filter body 19, gutter 30 diverts any incoming fluid that may contact the back portion of filter body 19 toward one end of gross filter 19, as illustrated by flow pathway A2. Guide 24 is provided for further channeling incoming fluid toward one end of bottom panel 18 so as to inhibit the total blockage of panel 18 by continually wetting a portion of filter body 18 which prevents drying and caking of fluid over filter matrix 34.

As incoming fluid is channeled through filter body 19 it may follow basically one of two flow pathways as incoming fluid is filtered. Flow pathways A3 and A6 show filtration of incoming fluid through first and second side panels 14 and 16, respectively, when total blockage of bottom panel 18 occurs, while flow pathway A4 illustrates the filtration of incoming fluid through the back panel 12 under similarly blocked circumstances. Finally, flow pathway A5 illustrates the pathway of incoming fluid through bottom panel 18.

Although most of the incoming fluid is filtered through bottom panel 18 due to the channeling effect of the guide 24 and splash guard 86, the angled orientations of first and second side panels 14 and 16 and back panel 12 provide secondary filtration areas when the bottom panel 18 becomes clogged with large particulate matter which are retained inside the filter body 19, thereby preventing fluid flow therethrough for filtering incoming fluid. In such instances, the above-identified secondary filtration areas provide unimpeded filtration of incoming fluid when the bottom panel 18 becomes blocked. Flow pathways A3, A4 and A6 illustrate the potential alternate pathways that incoming fluid may follow when flow pathway A5 is interrupted due to blockages that may occur at bottom panel 18.

Figure 9:
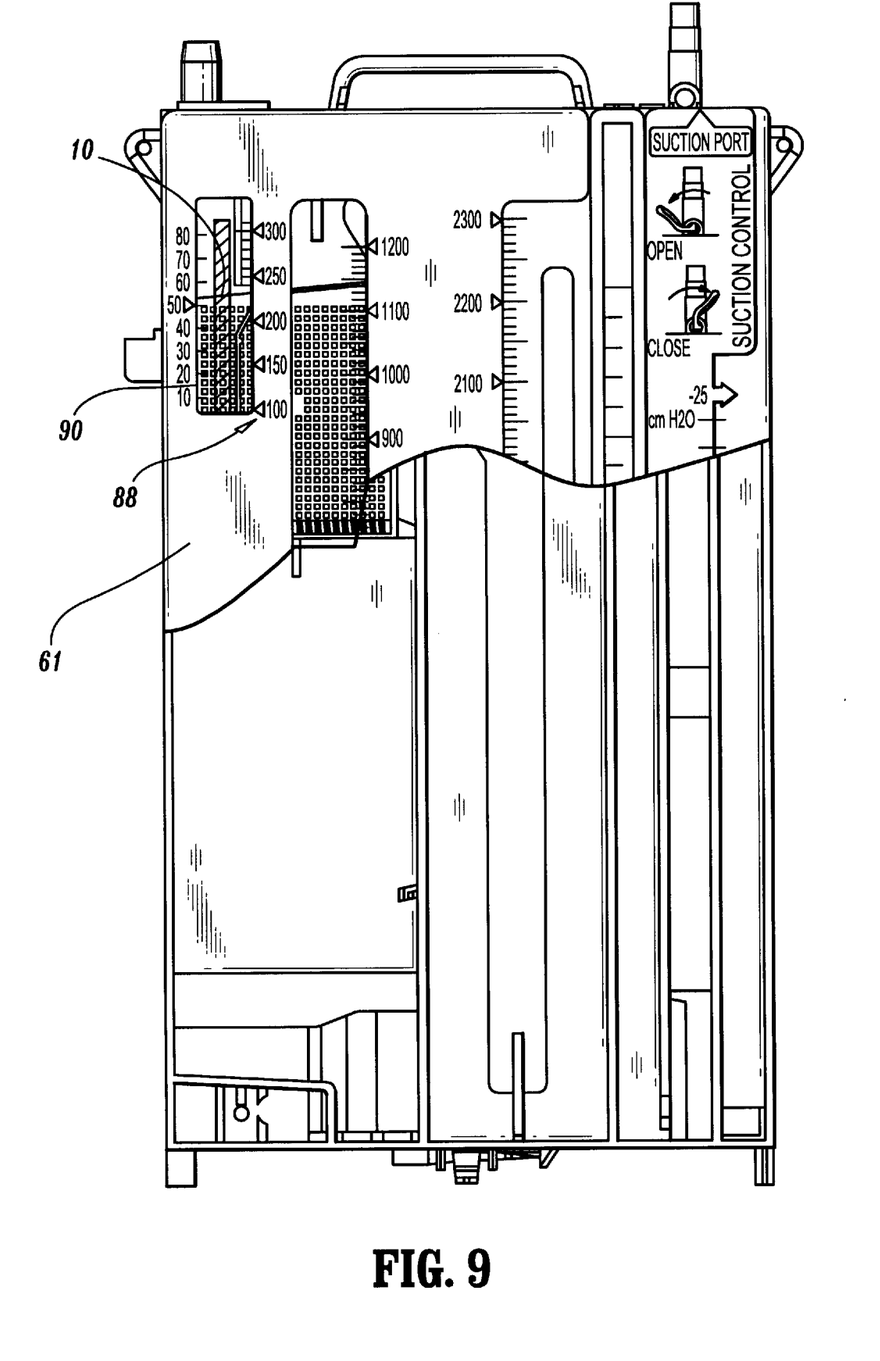
FIG. 9 is a perspective view of the Chest Drainage Unit illustrating the measuring indicia provided on the front wall for visually measuring the volume of large particulate matter retained inside the gross filter according to the present invention.

Referring to FIG. 9, measuring indicia 88 used to visually ascertain the volume of large particulate matter retained inside gross filter 10 is illustrated. The measuring indicia 88 is provided on the front wall 61 of CDU 11 adjacent to a window 90 which shows the interior portion of gross filter 10 so that a nurse or other medical personnel may visually ascertain the volume of large particulate matter retained inside filter body 19. Preferably, measuring indicia 88 is a combination of numerical indicators with respective markers that highlight specific volume levels, although numerical indicators or markers alone may be used. During manufacturing indicia 88 may be silk screened directly on the front wall 61, as in the preferred embodiment, or in the alternative, a label may be applied to the front wall 61 using a suitable adhesive.

Figure 10:
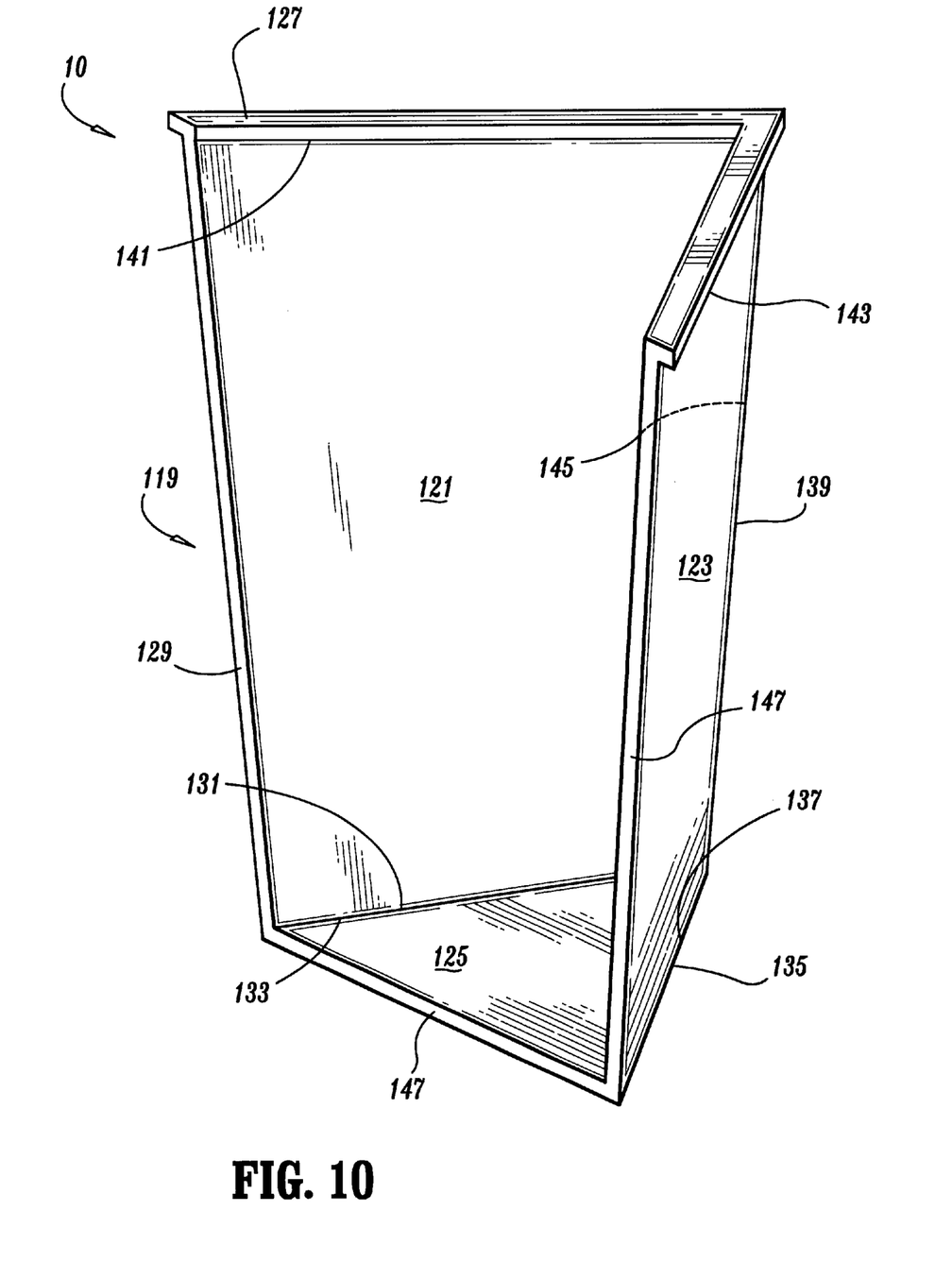
FIG. 10 is a perspective view of an alternative embodiment of the gross filter shown in FIG. 1 according to the present invention.
Figure 11:
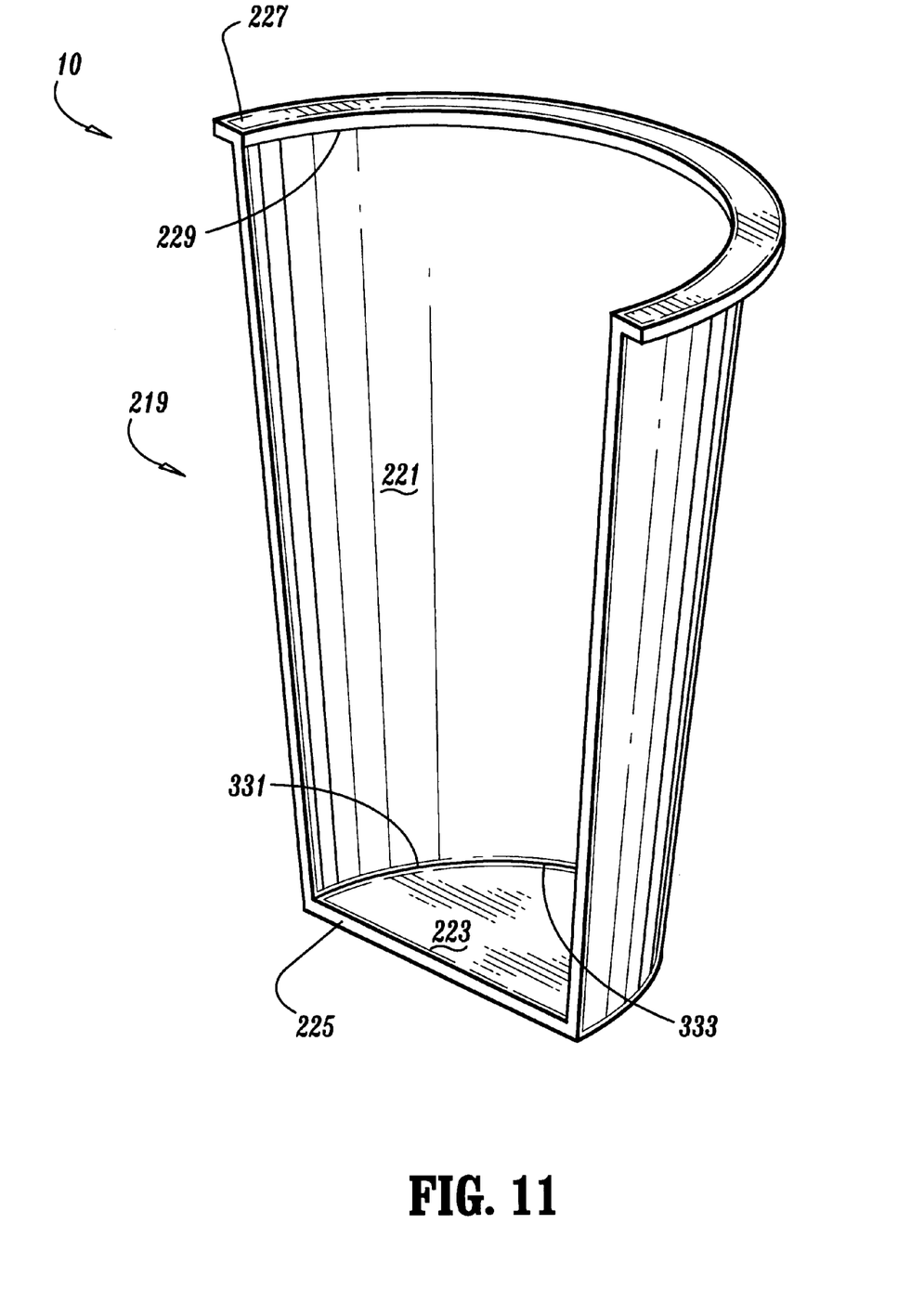
FIG. 11 is a perspective view of another alternative embodiment of the gross filter shown in FIG. 1 according to the present invention.

FIGS. 10 and 11 illustrate alternative shapes of filter body 19 according to the present invention. As shown in FIG. 10, filter body 119 has a triangular shape that channels incoming fluid flow in order to prevent total blockage of body 119 while permitting a clear view of the volume of gross particular matter retained therein.

Filter body 119 comprises a generally rectangular-shaped first side panel 121 defined by angled base edge 131, head edge 141, free edge 129 and inner edge 145. Preferably, base edge 131 is set a 10 degree angle with respect to edge 141, although the angle may range from 1 degree to 15 degrees.

Base edge 131 may be integrally formed with or attached to first side edge 133 of bottom panel 125. Bottom panel 125 has a generally triangular shape and is defined by first side edge 133, second side edge 135 and free edge 147. Similar to filter body 19, bottom panel 125 of filter body 119 is set at an angle so that the entire panel 125 slants slightly downward from the point where first and second side edges 131 and 135 meet to free edge 147. This downward slant of bottom panel 125 ensures that blood clots and other gross particular matter gravity flows toward, and accumulates at, the front portion of filter body 119.

Second side edge 135 is integrally formed with or attached to base edge 137 of second side panel 123. Second side panel 123 has a generally rectangular shape and is defined by angled base edge 135, inner edge 139, head edge 143 and free edge 147. Preferably, base edge 135 is set at the same 10 degree angle as base edge 131 of first side panel 121, although the angle may range from 1 degree to 15 degrees. Inner edge 139 may be integrally formed with or attached to inner edge 145 of first side panel 121. Both head edges 141 and 143 of first and second side panels 121 and 123, respectively, include a retaining ledge 127 which may be integrally formed with or attached thereto. Retaining ledge 127 provides a means for retaining filter body 119 inside the collection chamber 13 by engaging ledge 127 to a support member (not shown) provided along the wall of first subchamber 68.

Referring to FIG. 11, filter body 219 has a semi-circular/conical shape with the conical configuration of body 219 slightly tapered inward. Filter body 219 comprises a semi-circular panel 221 that is defined by free edge 225 which forms a generally rectangular shape with an open top portion. Semi-circular panel 221 is defined by head edge 229, free edge 225 and base edge 331. Head edge 229 forms a semi-circular shape with a similarly shaped retaining ledge 227 integrally formed with or attached to edge 229. Retaining ledge 227 also provides a means for retaining filter body 219 inside collection chamber 13 by engaging ledge 227 to a support member (not shown) provided along the wall of first subchamber 68. Base edge 331 may be integrally formed with or attached to a generally semi-circular shaped head edge 333 of bottom panel 223. Bottom panel 223 has a generally semi-circular shape defined by head edge 333 and free edge 225. Similar to filter body 119, bottom panel 223 of filter body 219 is set at an angle so that the entire panel 223 slants slightly downward toward free edge 225. This downward slant of bottom panel 223 ensures that blood clots and other gross particular matter gravity flows toward, and accumulates at, the front portion of filter body 219.

It should be understood from the foregoing that, while particular embodiments of the invention have been illustrated and described, various modifications can be made thereto without departing from the spirit and scope of the invention. Therefore, it is not intended that the invention be limited by the specification; instead, the scope of the present invention is intended to be limited only by the appended claims.

What is claimed is:

1. A medical device including a filter for filtering a fluid in a medical device, the medical device comprising a vessel including a first and second side walls, a back wall, a front wall, a bottom wall and a top wall, the medical device including a collection chamber having at least two subchambers, one of at least two subchambers including a first side wall, back wall top wall and a partition wall having a port interposed between at least two subchambers, the collection chamber being in fluid communication with a patient through an inlet port for the collection of incoming fluid from a patient, the filter comprising:

a filter body having a bottom panel interposed between at least two side panels, an open front and top portions, wherein said bottom panel and said at least two side panels each include a front edge which sealingly abuts said front wall of said vessel, said filter body being disposed near or adjacent to the inlet port of the collection chamber for receiving fluid through said open top portion, said open front portion permitting an accurate visual measurement of any accumulation of particulates retained inside said filter body;

wherein the filter body comprises first and second side panels, a back panel and a bottom panel, wherein each of said panels includes a filter matrix, the filter matrix having a two dimensional continuous pattern of geometric shapes.

2. The medical device according to claim 1, wherein the front wall of the medical device includes indicia for visually measuring the amount of particulates retained inside said filter body.

3. The medical device according to claim 2, wherein the particulates are blood clots.

4. The medical device according to claim 1 wherein at least a portion of said first side panel lies in a first plane and at least a portion of said second side panel lies in a second plane, said first and second planes not being parallel.

5. The medical device according to claim 1, wherein either of said first or said second side panels has a second filter at a top portion thereof for filtering fluid that overflow from said open portion into said second subchamber.

6. The medical device according to claim 1, wherein said bottom panel forms an opening adapted to receive a conduit therethrough.

7. The medical device according to claim 1, wherein said first and second side panels each include a spacing means for spacing part said first and second side panels from the first side wall and the partition wall respectively.

8. The medical device according to claim 1, wherein said first and second side panels comprise first and second edges respectively, said first and second edges being adjacent or attached to the front wall of the medical device.

9. A medical device including a filter for filtering fluid in a medical device, the medical device comprising a vessel including first and second side walls, a back wall, a front wall, a bottom wall and a top wall, the medical device including a collection chamber having at least two subchamber, one of at least two subchambers housing the filter and including a first side wall, back wall, top wall, bottom wall and a port interposed between at least two subchambers, the collection chamber being in fluid communication with a patient through an inlet port for the collection of incoming fluid from a patient, the filter comprising:

a filter body having at least two adjacent panels which form a generally rectangular cross-section with open front and top portions, said open front having edges sealingly abutting said front wall of said vessel, said filter body being disposed near or adjacent to the inlet port of the collection chamber for receiving fluid through said open top portion, said open front portion permitting an accurate visual measurement of any accumulation of particulates retained inside said filter body;

wherein either of said first or said second side panels has a second filter portion for filtering incoming fluid that overflows from said open portion.

10. The medical device according to claim 9, wherein the front wall of the medical device includes indicia for visually measuring the amount of particulates retained inside said filter body.

11. The medical device according to claim 9, wherein each of said panels includes a filter matrix, the filter matrix having a two dimensional continuous pattern of geometric shapes.

12. The medical device according to claim 11, wherein at least a portion of said first side panel lies in a first plane and at least a portion of said second side panel lies in a second plane, said first and second planes not being parallel.

13. The medical device according to claim 12, wherein said first and second side panels each include a spacing means for spacing apart said first and second side panels from respective first and second side walls.

14. The medical device according to claim 9, wherein said bottom panel has a slanted orientation.

15. The medical device according to claim 9, wherein said first and second side panels comprise first and second edges respectively, said first and second edges being adjacent to the front wall of the medical device.

16. A medical device including a filter for filtering fluid in a medical device, the medical device comprising a vessel including first and second side walls, a back wall, a front wall, a bottom wall and a top wall, the medical device including a collection chamber having at least two subchambers, one of at least two subchambers including a first side wall, back wall, top wall, bottom wall and a port interposed between at least two subchambers, the collection chamber being in fluid communication with a patient through an inlet port formed through the vessel for ingress if incoming fluid from a patient, the filter comprising:

a filter body having a bottom panel interposed between at least two side panels, wherein said bottom panel and said at least two side panels each include a front edge which sealingly abuts said front wall of said vessel, said filter body having an open top portion an a guide member disposed therein, said filter body being disposed near or adjacent to the inlet port of the collection chamber for receiving fluid through said open top portion, said guide member channeling incoming fluid to one part of said filter body so as to continually wet said one part of said filter body to prevent drying and caking of fluid over a filter matrix.

17. The medical device according to claim 16, wherein said guide forms an angled portion adapted for channeling incoming fluid downward toward one end of said filter body.

18. The medical device according to claim 16, wherein at least a portion of said first side panel lies in a first plane and at least a portion of said second side panel lies in a second plane, said first and second planes not being parallel.

19. The medical device according to claim 16, wherein either of said first or said second side panels has a second filter at a top portion thereof for filtering fluid that overflows from said open portion into said second subchamber.

20. The medical device according to claim 16, wherein said bottom panel forms an opening adapted to receive a conduit therethrough.

21. The medical device according to claim 16, wherein said first and second side panels each include a spacing means for spacing apart said first and second side walls from the first side wall and the partition wall respectively.

* * * * *